US007001430B2

(12) United States Patent
Mills et al.

(10) Patent No.: US 7,001,430 B2
(45) Date of Patent: Feb. 21, 2006

(54) MATRIX COMPOSITION FOR HUMAN GRAFTS/IMPLANTS

(75) Inventors: C. Randal Mills, Tioga, FL (US); John R. Bianchi, Gainesville, FL (US); Michael R. Roberts, Gainesville, FL (US); David T. Cheung, Arcadia, CA (US); Chandrasekaran Nataraj, Gainesville, FL (US); John W. Howell, Jr., Gainesville, FL (US)

(73) Assignee: Regeneration Technologies, Inc., Alachua, FL (US)

( * ) Notice: Subject to any disclaimer, the term of this patent is extended or adjusted under 35 U.S.C. 154(b) by 141 days.

(21) Appl. No.: 10/754,310

(22) Filed: Jan. 9, 2004

(65) Prior Publication Data

US 2005/0152880 A1    Jul. 14, 2005

(51) Int. Cl.
A61F 2/08 (2006.01)
A61F 2/02 (2006.01)
A61K 38/17 (2006.01)
A61K 35/34 (2006.01)

(52) U.S. Cl. .................. 623/14.13; 424/423; 424/424; 424/548; 514/12

(58) Field of Classification Search ............. 623/14.13; 424/423, 548, 424; 514/12
See application file for complete search history.

(56) References Cited

U.S. PATENT DOCUMENTS

| 3,855,196 | A | * | 12/1974 | Matsukawa et al. ........ 530/300 |
| 6,659,995 | B1 | | 12/2003 | Taheri |
| 2002/0119177 | A1 | | 8/2002 | Bowman et al. |
| 2003/0113301 | A1 | * | 6/2003 | Edge et al. .............. 424/93.21 |

2003/0180266 A1    9/2003    McKay et al.

FOREIGN PATENT DOCUMENTS

| WO | WO 96/39035 A | 12/1996 |
| WO | WO 01/78754 A | 10/2001 |

OTHER PUBLICATIONS

Djurhuus et al., "Methodological Aspects of measuring human skeletal muscle electrolyte content and ouabain binding capacity," Anal Biochem 260:218-222, 1998.*

Journal of Bone and Mineral Research, Apr. 2003, vol. 18, No. 4, p. 705, "In Vitro and In Vivo Synergistic Interactions Between the Runx2/Cbfa1 Transcription Factor and Bone Morphogenetic Protein-2 in Stimulating Osteoblast Differentiation", Shuying Yang, Daoyan Wei, Dian Wang, Mattabhorn Phimphilai, Paul H. Krebsbach and Renny T. Franceschi.

Djurhuus M S et al.: "Methodological aspects of measuring human skeletal muscle electrolyte content and ouabain binding capacity." Analytical Biochemistry. Jul. 1, 1998, vol. 260, No. 2., Jul. 1, 1998, pp. 218-222, XP002296843 ISSN: 0003-2697.

* cited by examiner

Primary Examiner—Jon Weber
Assistant Examiner—Rosanne Kosson
(74) Attorney, Agent, or Firm—Donald I. Pochopien; McAndrews, Held & Malloy

(57) ABSTRACT

The present invention is directed to an intermediate composition for producing a muscle tissue matrix suitable for implantation in humans, comprising shredded, allogeneic human muscle tissue that has been combined with an aqueous carrier, preferably a biocompatible acid solution, to form a muscle tissue slurry having a viscosity within the range of 1 centistoke to 20,000 centistokes measured at 25° C. In another aspect, the present invention is directed to a tissue implant comprising a human muscle tissue matrix.

21 Claims, 4 Drawing Sheets

MATRIX COMPOSITION FOR HUMAN GRAFTS/IMPLANTS

BACKGROUND OF THE INVENTION

The present invention is directed to the field of biocompatible matrices for human implantation. More particularly, the present invention is directed to an intermediate composition for forming an allogeneic biocompatible matrix that is capable of carrying other implantable materials or that can be formed into a plurality of tissue implants having different properties and different shapes. The present invention is useful because it provides an intermediate composition that is versatile in its ability to be formulated into a variety of implants or grafts that are useful in the treatment of a variety of medical conditions in patients. In another aspect, the present invention is directed to the implant/graft that is formed from the intermediate composition of the present invention.

In the field of biomedical implants, devices have been made that range far afield from the biological components found in the human body. For example, many devices that are intended as bone substitutes are made from metals such as titanium, or biocompatible ceramics. A problem in such instances is that they have different material properties than the host tissue causing the devices to loosen at the interface between the host tissue and the device itself.

One solution to the problem was the use of allograft bone in place of metal or ceramic implants. Under the proper conditions and under the influence of osteogenic substances, implants made of allograft bone can act as the scaffolding for remodeling by the host. Such implants function by being both structurally and biologically similar to the host tissue. Further, they allow cellular recruitment through the natural openings in the matrix and allow the graft to be replaced by natural host bone. While allograft bone is very useful, it is limited by the intended clinical use. Thus, it is particularly useful for spinal fusions where the spacings between the vertebrae are relatively fixed and well known. However, injuries come in a variety of shapes and sizes which presents a logical limitation on the availability of an ideal graft to fill the defect. Moreover, availability, donor demographics and cost further limit the usefulness of allograft bone. Accordingly, there is a need in the art for an implantable biocompatible matrix that can be formulated into a variety of shapes and sizes and that can act as scaffolding to allow the infiltration of native regenerative cells that will lay down a natural replacement structure in the shape of the implant.

Another example area where biocompatible implants are important is in replacement skin for burn victims. Histocompatibility, remodeling and safety are considerable problems in utilizing allograft skin. To avoid this problem and the shortage of viable donor skin, a surgeon often removes skin from another part of the patient and transplants it to the area of need. While such skin is non-antigenic, it causes significant morbidity to the patient at the site of removal. Moreover, depending upon the size of the wound or burn, there may not be sufficient skin on the patient to satisfy the need. To alleviate this problem, at least one company will culture the patient's skin cells on a collagen matrix to form a transplantable layer of skin. However, the culture time is relatively extensive and the patient's wound or burn is exposed while awaiting the graft. Moreover, the grafts generated in this way do not mimic normal skin, which is composed of multiple cell types and structures. Accordingly, there is a need in the art for an implantable biocompatible matrix that can be formulated into a sheet and cut to size and that can act as scaffolding to allow the infiltration of a variety skin cells from adjacent tissue that will lay down a compatible and natural replacement structure in the shape of the implant, while absorbing the implant itself.

The present invention describes the preparation of a matrix from biological tissue that has the ability to be formulated into a variety of forms and shapes that can participate in the correction of a variety of pathologies such as those described above.

BRIEF SUMMARY OF THE INVENTION

The applicants have discovered an intermediate composition that, as is or when dried, provides a biocompatible, non-antigenic matrix and scaffolding material for tissue regeneration in humans. In its simplest form, the present invention is directed to an intermediate composition for producing a matrix suitable for implantation in humans, comprising defatted, shredded, allogeneic human muscle tissue that has been combined with an aqueous carrier to form a muscle tissue slurry having a viscosity within the range of 1 centistoke to 20,000 centistokes when measured at 25° C. Typically, the muscle tissue slurry has a viscosity within the range of 1 centistoke to 10,000 centistokes when measured at 25° C.; more typically, the muscle tissue slurry has a viscosity within the range of 1 centistoke to 5,000 centistokes when measured at 25° C.

The muscle tissue slurry of the present invention is also characterizable in terms other than viscosity. Specifically, the muscle tissue slurry is characterized instead by the ratio of aqueous carrier (volume in milliliters) to dry weight of muscle (grams). The aqueous carrier is acidic, basic or neutral. Preferably, the aqueous carrier is an aqueous acidic solution ("an acid"). Typically, the ratio of volume of acid (milliliters) to dry weight of muscle (grams) is within the range of 100:1 to 10:1; more typically within the range of 80:1 to 20:1; most typically within the range of 70:1 to 30:1. The choice of the ratio of aqueous carrier to muscle tissue determines the viscosity of the slurry and the choice is based upon the ultimate application of the slurry. The muscle tissue slurry of the present invention was used to make the various tissue implants and grafts (collectively "implants") disclosed further herein.

Although autogeneic muscle can be used in the intermediate composition of the present invention, the source of the muscle is typically donor muscle that is obtained from cadavers and thus, the muscle is allogeneic. While the present invention is discussed herein in terms of an allogeneic human muscle source and being used for preparing an tissue implant for humans, any mammal may be used as the muscle donor and the resulting slurry used to prepare a xenogeneic implant for use in a human or in another species of mammal. In the examples herein, the applicants disclose that they ectopically implanted a tissue matrix (derived from human muscle) in a rat and the tissue matrix was resorbed over a period of time without inducing an inflammatory response. This establishes the functionality of the matrix as a resorbable and biocompatible tissue scaffold even when implanted (as a xenograft) in a different species. Thus, there is evidence that the intermediate composition of the present invention would produce an acceptable tissue matrix even when made from xenograft muscle tissue.

In a preferred embodiment of the present invention, chunks of the allogeneic human muscle tissue were defatted prior to being shredded. Suitable methods for defatting tissue are well known in the art. In the present case, the applicants utilized the assignees' well known method for defatting tissue, which also removes blood, cellular debris, and soluble and antigenic proteins, by cyclically subjecting the muscle tissue to alternating pressure and vacuum in the presence of a series of solvents, such as isopropyl alcohol, hydrogen peroxide and detergents. These methods are disclosed in full detail in assignee's U.S. Pat. No. 6,613,278, entitled "Tissue Pooling Process," which issued to Mills et al., on Sep. 2, 2003; U.S. Pat. No. 6,482,584, entitled "Cyclic implant perfusion cleaning and passivation process," which issued to Mills, et al. on Nov. 19, 2002; and U.S. Pat. No. 6,652,818, entitled "Implant Sterilization Apparatus," which issued to Mills et al., on Nov. 25, 2003, all of which are incorporated herein by reference in their entirety. After being subjected to the process of the above patents, the allogeneic muscle tissue was defatted, nonantigenic and substantially free of soluble protein.

In a more preferred embodiment, the defatted allogeneic human muscle tissue was dried, more preferably by lyophilization, to facilitate further processing, such as shredding. The lyophilization process need not remove all of the water. While the water content of the chopped allogeneic muscle can vary, it is typically dried to about 3% moisture content by weight. It is especially preferred that the allogeneic human muscle tissue be defatted prior to lyophilization.

The defatted and dried muscle tissue is shredded to a coarse fiber prior to digestion with a biocompatible acid. The shredded muscle tissue is digested with a biocompatible acid to produce the intermediate composition of the present invention. The biocompatible acid is either a biocompatible organic acid or a biocompatible inorganic acid. Preferably, a suitable biocompatible acid is selected from the group consisting of acetic acid, citric acid, formic acid, hydrochloric acid, phosphoric acid, phosphorous acid and sulfuric acid. More preferably, the biocompatible acid is an organic acid; most preferably, the organic acid is acetic acid.

The intermediate composition of the present invention is implantable in liquid form. In another embodiment, it is dried to prepare a variety of tissue implants.

Thus, in its second aspect, the present invention is directed to a tissue implant suitable for treating an injury or a surgical or medical condition in a human patient, wherein the tissue implant comprises a matrix of digested allogeneic human muscle. In this embodiment, the matrix of digested allogeneic human muscle comprises from about 1% to about 100% of the final weight of the implant, more typically from 15% to about 95% of the final weight of the implant, even more typically from 25% to about 85% of the final weight of the implant.

In another embodiment, the tissue implant comprising a matrix of digested allogeneic human muscle having demineralized bone matrix (DBM), cortical cancellous chips (CCC) and/or allogeneic tendon dispersed within the matrix. In one variation of the above embodiment, the DBM or CCC or both are dispersed equally or randomly throughout the matrix. In another variation, the DBM or CCC or both are sandwiched between layers of the matrix to form a laminate implant. When the tissue implant of the present invention contains DBM, the resulting tissue implant is osteogenic and particularly suited for repairing bone. When the tissue implant contains tendon, it is much tougher than the digested human muscle matrix alone and is particularly suited as a dressing for a wound or burn that will become infiltrated with skin cells and allow for development of a replacement skin layer that will cover the wound or burn. In this embodiment, the matrix of digested allogeneic human muscle comprises from about 1% to about 100% of the dry weight of the tissue implant, more typically from 15% to about 95% of the dry weight of the tissue implant, even more typically from 25% to about 85% of the dry weight of the tissue implant.

The implant/graft of the present invention comprising a matrix of digested allogeneic human muscle were made in the shape of a strip, a sheet, a molded 3D shaped object, a sponge, and a gasket. Any of these objects may include a cavity, a pouch, a hole, a post, a hook, or a suture. The one or more holes or cavities are optionally molded into implants or cut into them after the implant is formed. These (human muscle based) implants were implanted at an ectopic site in an athymic rat to test for resorption and biocompatibility. The implants were resorbed in the rat models and did not invoke an inflammatory response.

Preferably, the resulting intermediate composition (the digested allogeneic human muscle slurry) of the present invention is degassed, by pouring the slurry into plates or tubes, and centrifuging them to eliminate any entrapped air and produce a higher density slurry. At this point, the slurry may be finally sterilized, and the sterilized slurry injected to a site of injury in a patient in need of treatment by a scaffolding agent.

Alternatively, the slurry is poured into a mold for formation of an implantable tissue matrix of any size or shape. As noted above, the slurry can be combined with other agents, such as DBM, CCC or a collagen (e.g., tendon, fascia) slurry before being poured into the mold. To produce an implantable film, a thin layer of the slurry is poured in a flat plate and the slurry is either air dried, air dried with positive airflow, or dried in an oven, preferably a convection oven. To produce a sponge, a gasket or an implantable shape, the slurry (neat or amended) is poured into a mold of the appropriate shape, frozen (to retain its size), and lyophilized. The resulting dried implantable film or shape is then ready for packaging and final sterilization. Thus, in another embodiment, the present invention is directed to a method for making a tissue implant comprising the above method.

When the tissue implants of the present invention contained DBM, CCC or tendon, these components were combined with a lower viscosity embodiment of the intermediate composition of the present invention because the addition of these components increased the viscosity of the matrix, making it more difficult to manipulate.

Prior to use, the freeze dried tissue implants are removed from their sterile packaging and rehydrated by contacting them with water, saline, blood, plasma, a buffered solution, or any other suitable liquid.

The tendon that is used in the tissue implants of the present invention is processed the same as the human muscle. It is chopped into pieces, defatted, freeze dried (lyophilized), shredded into a coarse fiber, and acid digested to provide a viscous tendon digestate that is suitable for combining with the acid digested allogeneic muscle (intermediate composition) of the present invention. The ratio of tendon digestate to intermediate composition ranges from 1:99 to 99:1. Typically, the range is 10:90 to 90:10; more typically, the range is 25:75 to 75:25. While the above discussion is in relation to "tendon," which is a preferred source of collagen for this invention, it is intended that any collagen source be used, including fascia.

BRIEF DESCRIPTION OF SEVERAL VIEWS OF THE DRAWINGS

FIG. 3A. is a side view. In FIG. 3B, the implant is rotated 90° to show the hole that was molded in the center.

In FIG. 4A, the film was formed from the muscle slurry without an additive. In FIG. 4B, the film was made from a mixed slurry comprising a 50:50 ratio of muscle tissue to tendon tissue.

DETAILED DESCRIPTION OF THE INVENTION

Figure 1:
FIG. 1 is a photograph showing the fluffy fibrous texture of shredded, defatted allogeneic human muscle for use in making the intermediate composition (muscle slurry) of the present invention.
Figure 2A:
FIGS. 2A–2C are photographs of tissue implants in the form of a sponge that were made from the muscle slurry of the present invention.
Figure 2B:
Figure 2C:
Figure 3A:
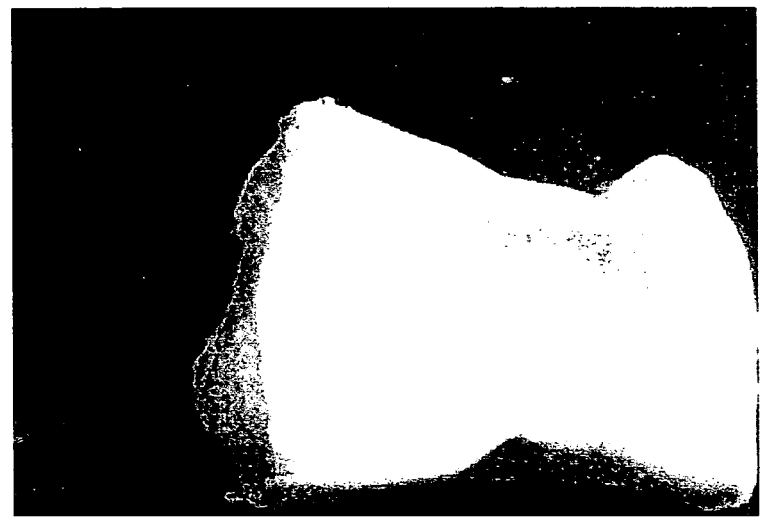
FIGS. 3A–3B are photographs of a three-dimensional molded tissue implant made from the muscle slurry of the present invention.
Figure 3B:
Figure 4A:
FIGS. 4A and 4B are photographs of tissue implants/grafts in the form of a thin film that were made from the muscle slurry of the present invention.
Figure 4B:
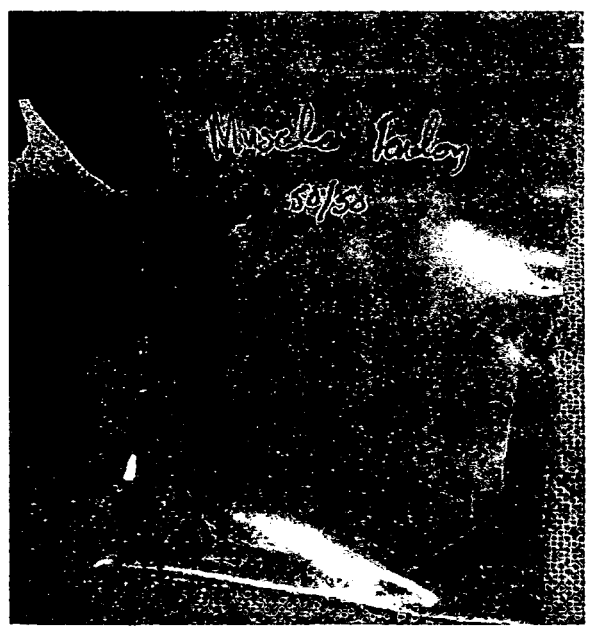

The present invention has multiple embodiments. In its first embodiment, the present invention is directed to an intermediate composition that, as is or when dried, provides a biocompatible, non-antigenic matrix and scaffolding material for tissue regeneration in humans. In its simplest form, the present invention is directed to an intermediate composition for producing a tissue matrix suitable for implantation in humans, comprising shredded, defatted, allogeneic human muscle tissue that has been combined with an aqueous carrier to form a muscle tissue slurry having a viscosity within the range of 1 centistoke to 20,000 centistokes when measured at 25° C. Typically, the muscle tissue slurry has a viscosity within the range of 1 centistoke to 10,000 centistokes when measured at 25° C.; more typically, the muscle tissue slurry has a viscosity within the range of 1 centistoke to 5,000 centistokes when measured at 25° C.

The muscle tissue slurry of the present invention is also characterizable in terms other than viscosity. Specifically, the muscle tissue slurry is characterized instead by the ratio of the volume of aqueous carrier (milliliters) to dry weight of muscle (grams). The aqueous carrier is acidic, basic or neutral. Preferably, the aqueous carrier is an aqueous acidic solution ("an acid"). Typically, the ratio of acid (volume) to dry weight of muscle (grams) is within the range of 100:1 to 10:1; more typically within the range of 80:1 to 20:1; most typically within the range of 70:1 to 30:1. The choice of the ratio of acid to protein determines the viscosity of the slurry and the choice is based upon the ultimate application of the slurry. The muscle tissue slurry of the present invention was used to make the various tissue implants and grafts (collectively "implants") disclosed further herein.

The viscosity of the muscle tissue slurry (i.e., intermediate composition) ranges between slightly greater than the viscosity of water to almost solid.

Although autogeneic muscle can be used in the intermediate composition of the present invention, the source of the muscle is typically donor muscle that is obtained from cadavers and thus, the muscle is allogeneic. While the present invention is discussed herein in terms of an allogeneic human muscle source and being used for preparing a tissue implant for humans, any non-human mammal may be used as the muscle donor and the resulting slurry used to prepare a xenogeneic implant for use in a human or in another species of mammal. Preferred xenographic muscle sources are porcine and bovine. Pigs are currently being used to generate minimally antigenic hearts suitable for implantation as living heart transplants in humans. In the examples herein, the applicants disclose that they ectopically implanted into a rat a tissue matrix (in the form of a sponge) that was derived from human donor muscle and the tissue matrix was resorbed over a period of time without inducing an inflammatory response. This establishes the functionality of the tissue matrix as a biocompatible resorbable tissue scaffold even when implanted (as a xenograft) in a different species. Thus, there is evidence that the intermediate composition of the present invention would produce an acceptable tissue matrix even when made from xenograft muscle tissue.

In a preferred embodiment of the present invention, the muscle tissue is defatted prior to or after being shredded. Preferably, it is defatted prior to being shredded. In this embodiment, the donor muscle is cut into chunks of sufficiently small size (e.g., 20 mm×20 mm) to allow the tissue to be easily defatted. Suitable methods for defatting tissue are well known in the art. Typically, this involves treating the tissue with a fat dissolving substance such as 60% to 90% alcohol in water. See U.S. Pat. No. 5,846,484, entitled "Pressure flow system and method for treating a fluid permeable workpiece such as a bone," which issued to Scarborough, et al. on Dec. 8, 1998. In the present case, the applicants utilized the assignees' well known method for defatting tissue, which also has the added benefit of removing blood, cellular debris, and soluble and antigenic proteins, by subjecting the muscle tissue to alternating cycles of pressure and vacuum in the sequential presence of solvents, such as isopropyl alcohol, hydrogen peroxide and a detergent. These methods are disclosed in full detail in assignee's U.S. Pat. No. 6,613,278, entitled "Tissue Pooling Process," which issued to Mills et al., on Sep. 2, 2003; U.S. Pat. No. 6,482,584, entitled "Cyclic implant perfusion cleaning and passivation process," which issued to Mills, et al. on Nov. 19, 2002; and U.S. Pat. No. 6,652,818, entitled "Implant Sterilization Apparatus," which issued to Mills et al., on Nov. 25, 2003, all of which are incorporated herein by reference in their entirety.

In a more preferred embodiment, the defatted allogeneic human muscle tissue was dried, more preferably by lyophilization, to facilitate further processing, such as shredding. The lyophilization process need not remove all of the water. While the water content of the chopped allogeneic muscle can vary, it is typically dried to about 3% moisture content by weight. It is especially preferred that the allogeneic human muscle tissue be defatted prior to lyophilization.

The defatted and dried muscle tissue was shredded to a coarse fiber. Shredding is accomplished by any commercial shredder. Suitable shredders include coffee grinders, food processors, and the like.

The shredded muscle tissue was mixed vigorously with a biocompatible acid to produce the muscle slurry that is the intermediate composition of the present invention. On a small scale, mixing was accomplished with a hand-held food processor. Mixing takes from 15 seconds to over two minutes and is dependent upon the amount of shredded protein and the volume of acid. Mixing should continue until the slurry has uniform consistency. After mixing, the slurry is preferably degassed. Degassing was accomplished by centrifugation, or possibly vacuum centrifugation.

The biocompatible acid is either a biocompatible organic acid or a biocompatible inorganic acid. Preferably, a suitable biocompatible acid is selected from the group consisting of acetic acid, citric acid, formic acid, hydrochloric acid, phosphoric acid, phosphorus acid and sulfuric acid. More preferably, the biocompatible acid is an organic acid; most preferably the organic acid is acetic acid.

The intermediate composition of the present invention is implantable in liquid form, such as by injecting into the patient at a site in need of restoration. In another embodiment, it is dried to prepare a variety of tissue implants.

Thus, in its second aspect, the present invention is directed to a tissue implant suitable for treating an injury or a surgical or medical condition in a human patient, wherein the tissue implant comprises a matrix of digested allogeneic human muscle. In this embodiment, the matrix of digested allogeneic human muscle comprises from about 1% to about 100% of the dry weight of the implant, more typically from 15% to about 95% of the dry weight of the implant, even more typically from 25% to about 85% of the dry weight of the implant.

In another embodiment, the tissue implant comprising a matrix of digested allogeneic human muscle having demineralized bone matrix (DBM), cortical cancellous chips (CCC) or allogeneic tendon dispersed within the matrix. In one variation of the above embodiment, the DBM or CCC or both are dispersed uniformly (and randomly) throughout the matrix. In another variation, the DBM or CCC or both are sandwiched between layers of the matrix to form a laminated tissue implant. When the tissue implant of the present invention contains DBM, the resulting implant is osteogenic and particularly suited for repairing bone.

When the tissue implant contains tendon, it is much tougher than the digested human muscle matrix alone and is particularly suited as a dressing for a wound or burn that will become infiltrated with skin cells and allow for development of a replacement skin layer that will cover the wound or burn. In this embodiment, the tendon comprises from 1% to about 99% of the dry weight of the implant, more typically from 15% to about 75% of the dry weight of the implant, even more typically from 25% to about 50% of the dry weight of the implant.

The implant/graft of the present invention comprising a matrix of digested allogeneic human muscle were made in the shape of a strip, a sheet, a molded 3D shaped object, a sponge, and a gasket. Any of these objects may include a cavity, a pouch, a hole, a post, a hook, or a suture. In making a strip, the dimensions are typically 200 mm by 300 mm and 1.5 mm thick, more typically from 10 mm by 100 mm and 1.0 mm thick, even more typically from 20 mm by 70 mm and 0.5 mm thick. For a sheet in this embodiment, the dimensions are typically 300 mm by 300 mm and 1.5 mm thick, more typically from 100 mm by 100 mm and 1.0 mm thick, even more typically from 70 mm by 70 mm and 0.5 mm thick. For a molded 3D shaped object in this embodiment, the dimensions are typically 100 mm by 100 mm and 25 mm thick, more typically from 50 mm by 70 mm and 20 mm thick, even more typically from 30 mm by 50 mm and 15 mm thick. For a sponge in this embodiment, the dimensions are typically 100 mm by 100 mm and 20 mm thick, more typically from 75 mm by 75 mm and 15 mm thick, even more typically from 50 mm by 50 mm and 5 mm thick. For a gasket in this embodiment, the dimensions are typically 100 mm by 100 mm and 15 mm thick, more typically from 50 mm by 50 mm and 5 mm thick, even more typically from 25 mm by 25 mm and 2.5 mm thick.

In a pilot study, prototype implants were resorbed into an ectopic site in an athymic nude rat model, without any signs of an inflammatory response. Specifically, an implant of Example 2, containing 20% DBM was implanted in abdominal muscle pouches of athymic nude rats using a modified Urist model. Urist, M. R., "Bone: Formation by Autoinduction," Science 160:893–894 (1965). The explants were retrieved four weeks later, processed, and evaluated histologically for evidence of new bone formation. The control implants containing only the sponge carrier were resorbed without evidence of inflammation. More significantly, the implants containing DBM demonstrated signs of new bone formation (endochondral ossification). Hence, the muscle tissue matrix of the present invention, under the influence of DBM, provided scaffolding for colonization by native restorative cells and the laying down of new bone.

Alternatively, the slurry is poured into a mold for formation of an implantable tissue matrix of any size or shape. As noted above, the slurry can be combined with other agents, such as DBM, CCC or a collagen (e.g., tendon, fascia) slurry before being poured into the mold. To produce an implantable film, a thin layer of the slurry is poured in a flat plate and the slurry is either air dried, air dried with positive airflow, or dried in an oven, preferably a convection oven. To produce a sponge, a gasket or an implantable shape, the slurry (neat or amended) is poured into a mold of the appropriate shape, frozen (to retain its size), and lyophilized. The resulting dried implantable film or shape is then ready for packaging and final sterilization.

Thus, in another embodiment, the present invention is directed to a method for making the intermediate composition (muscle tissue slurry) of the present invention comprising the steps of:
i. removing the fat and soluble proteins from allogeneic or xenographic mammalian muscle tissue;
ii. lyophilizing the muscle tissue from step (i);
iii. shredding the lyophilized muscle tissue; and
iv. mixing the shredded muscle tissue in an aqueous carrier to form a muscle tissue slurry having a viscosity within the range of 1 centistoke to 20,000 centistokes.

In yet another embodiment, the present invention is directed to a method for making an implantable tissue comprising the steps of:
i. removing the fat and soluble proteins from allogeneic or xenographic mammalian muscle tissue;
ii. lyophilizing the muscle tissue from step (i);
iii. shredding the lyophilized muscle tissue;
iv. mixing the shredded muscle tissue in an aqueous carrier to form a muscle tissue slurry having a viscosity within the range of 1 centistoke to 20,000 centistokes;
v. transferring the muscle tissue slurry to an appropriate shaped mold: and
vi. drying the slurry in the mold to form the correspondingly shaped tissue implant.

When the tissue implants of the present invention contained DBM, CCC or tendon, these components were combined with a lower viscosity embodiment of the intermediate composition of the present invention because the addition of these components increased the viscosity and workability of the matrix.

Prior to use, the freeze dried tissue implants are removed from their sterile packaging and rehydrated by contacting them with water, saline, blood, plasma, a buffered solution, or any other suitable liquid.

The tendon that is used in the tissue implants of the present invention is processed the same as the allogeneic human muscle. It is chopped into pieces, defatted, freeze dried (lyophilized), shredded into a coarse fiber, and acid digested to provide a viscous tendon digestate that is suitable for combining with the acid digested allogeneic muscle (intermediate composition) of the present invention. The ratio of tendon digestate to intermediate composition ranges from 1:99 to 99:1. Typically, the range is 10:90 to 90:10; more typically, the range is 25:75 to 75:25. While the above discussion is in relation to "tendon," which is a preferred source of collagen for this invention, it is intended that any collagen source be used, including fascia. The collagen source is xenogeneic or allogeneic. Preferably, it is allogeneic.

EXAMPLE 1

Preparation of a Slurry of Allogeneic Human Muscle

Skeletal muscle was removed from a donor cadaver and cut into chunks (20 mm×20 mm). The chunks of skeletal muscle were defatted, deantigenized and soluble protein was removed by subjecting the muscle tissue to cyclically alternating pressure and vacuum in the sequential presence of the isopropyl alcohol, hydrogen peroxide and a detergent. The method is fully described in assignee's U.S. Pat. No. 6,613,278, entitled "Tissue Pooling Process," which issued to Mills et al., on Sep. 2, 2003; U.S. Pat. No. 6,482,584, entitled "Cyclic implant perfusion cleaning and passivation process," which issued to Mills, et al. on Nov. 19, 2002; and U.S. Pat. No. 6,652,818, entitled "Implant Sterilization Apparatus," which issued to Mills et al., on Nov. 25, 2003, all of which are incorporated herein by reference in their entirety. After the above cleansing process, the defatted and non-antigenic muscle tissue was lyophilized to remove the moisture. The lyophilization procedure was a standard 17-hour program. The dried chunks were shredded and chopped in a grinder. The processing time varied from 5 seconds to 2 minutes depending upon the amount of lyophilized muscle being processed, dryness and starting size. At this stage, the shredded muscle tissue looks like fluffed fibers. The shredded muscle tissue were weighed and then combined with a predetermined amount of 10% or 20% aqueous acetic acid according to the table below:

TABLE 1

Ratios of Acetic Acid (ml) to weight of dry muscl (g)

| Acid | Muscle (g) Acid:muscle | Muscle (g) Acid:muscle | Muscle (g) Acid:muscle |
|---|---|---|---|
| 10% acetic acid | 0.5 g 46:1 | 0.75 g 34:1 | 1 g 22:1 |
| 20% acetic acid | 0.5 g 46:1 | 0.75 g 34:1 | 1 g 22:1 |

The combined acid solution and muscle tissue were mixed with a high speed mixer until a uniform gel (i.e., slurry) was formed. Mixing took between 15 seconds to more than 2 minutes depending upon the acid concentration, amount of muscle tissue and volume of acid solution.

The above described slurry was used alone or combined with another component to make a tissue implant of the present invention. The lower viscosity (more dilute) slurries were preferred when making pourable/flowable films. The lower to intermediate viscosity slurries were more desirable when being combined with DBM or CCC or tendon, each of which thickened the slurry.

EXAMPLE 2

Formulation Comprising the Slurry of Example 1 and DBM

The slurry of Example 1 was degassed via centrifugation. After the degassing, the slurry was transferred to a mixing bowl. DBM was added and mixed to uniformity at ratios of 0.1%, 1%, 5%, 10%, 20% and 30% (DBM weight to slurry weight).

A portion of each of the above slurries containing the DBM were poured into molds and allowed to dry at room temperature with positive airflow. The dried products produced a series of muscle based tissue implants in the form of films with the differing amounts of DBM embedded therein.

A second portion of the slurries from above was poured into molds, frozen, and lyophilized. The dried products produced a series of sponge-like tissue implants having increasing amounts of DBM therein.

EXAMPLE 3

Formulation Comprising the Slurry of Example 1 and CCC

The slurry of Example 1 was degassed via centrifugation. After the degassing, the slurry was transferred to a mixing bowl. CCC was added and mixed until uniform at a ratio of 50% (CCC volume to slurry volume). The slurry containing CCC was poured into a mold, frozen, and lyophilized. This dried product produced a tissue implant in the form of a sponge with CCC imbedded therein.

The degassed slurry from above was transferred to a mixing bowl, where 60% CCC (CCC volume to slurry volume) and 10% DBM (DBM volume to slurry volume) were added to the degassed slurry with mixing. Mixing continued until a uniform appearing mixture was formed. The slurry was poured into a cube shaped mold, frozen, and lyophilized. This dried product produced a cube shaped tissue implant having CCC and DBM imbedded therein.

EXAMPLE 4

Formulation Comprising the Slurry of Example 1 and a Slurry of Tendon

The slurry from Example 1 was degassed via centrifugation. After degassing, the slurry was transferred to a series of three (3) mixing bowls. Using allogeneic human tendon, a tendon slurry was made in the exact same manner as the muscle slurry. After the solubilized tendon slurry was degassed, a portion of it was added to each of the three (3) mixing bowls. The ratio of muscle to tendon in each of the three (3) bowls was 25:75, 50:50 and 75:25 (muscle volume: tendon volume), respectively. A portion of the tendon/skeletal slurry mixtures were poured into flat molds and allowed to dry at room temperature with positive airflow. Once dried, the three dried materials each produced a tissue implant in the form of a film.

Three identical tendon/skeletal muscle slurries were poured into molds, frozen, and lyophilized. The lyophilized frozen slurries produced tendon/skeletal muscle based implants in the form of a sponge.

EXAMPLE 5

Preparation of an Implantable Strip

A series of implantable strips were created from the films produced in Examples 1, 2, 3, and 4. Specifically, the dried films were cut into implantable strips that were 0.5 mm thick, 20 mm wide, and 70 mm long.

EXAMPLE 6

Preparation of an Implantable Sheet

An implantable sheet was created from the films produced in Example 1, 2, 3, and 4. The dried films either were left in the final shape of their molds, or were cut into sheets that were 0.5 mm thick, 70 mm wide and 70 mm long. Sheets were made that were also three dimensional, such as convex and concave spherical bodies. These implantable three dimensional films were made via rotational molding, vacuum centrifugation drying, room temperature drying, or room temperature drying with forced air, to a thin film in a three dimensional mold. Thicker sheets were produced in both two dimensional and three dimensional forms by successive reapplication of muscle tissue slurry, after drying of the preceding layer. In some cases DBM was added to the implant between this application of successive layers, to create a laminated tissue implant impregnated with DBM.

EXAMPLE 7

Preparation of an Implantable Sponge

A series of implantable sponges were made as specified in Examples 1, 2, 3, and 4 above. Using appropriate molds, the sponges were made in a square, circular, or hexagonal forms. The average thickness was 5 mm. The squares were as large as 50 mm by 50 mm. The circles had diameters as large as 90 mm. The hexagons were 40 mm per side.

EXAMPLE 8

Preparation of an Implantable Gasket

Using the slurry of Example 1, a gasket was made as a thinner version (2.5 mm) of the sponge in Example 7. The gasket was used in conjunction with a bone plate to tie together two model vertebral bodies in the laboratory.

EXAMPLE 9

Preparation of a Graftable Wound Dressing

The films from Example 4 were suitable for use as a wound dressing/skin graft. The films are hydrated before use with sterile saline until soft and pliable and then applied to the wound. Any excess film overhanging the wound is cut off with surgical scissors.

EXAMPLE 10

Biological Activity of an Ectopically Implanted Sponge in a Rat

The implant of Example 2, containing 20% DBM was implanted in abdominal muscle pouches of athymic nude rats using a modified Urist model. Urist, M. R., "Bone: Formation by Autoinduction," Science 160:893–894 (1965). Explants were retrieved four weeks later, processed, and evaluated histologically for evidence of new bone formation. Whereas control implants containing only the sponge carrier were resorbed without evidence of inflammation, those containing DBM demonstrated signs of new bone formation (endochondral ossification).

What is claimed is:

1. An intermediate composition for producing a matrix suitable implantation in humans, comprising shredded, allogeneic human muscle tissue that has been combined with an aqueous carrier to form a muscle tissue slurry having a viscosity within the range of 1 centistoke to 20,000 centistokes at 25° C., wherein said shredded allogeneic human muscle tissue is lyophilized and shredded into a coarse fiber prior to said digestion with a biocompatible acid.

2. The composition of claim 1 wherein said muscle tissue slurry having a viscosity within the range of 1 centistoke to 10,000 centistokes at 25° C.

3. The composition of claim 2, wherein said muscle tissue slurry having a viscosity within the range of 1 centistoke to 5,000 centistokes at 25° C.

4. The composition of claim 1 wherein said shredded allogeneic human muscle tissue is also defatted.

5. The composition of claim 1 wherein said aqueous carrier comprises a biocompatible acid selected from the group consisting of acetic acid, citric acid, formic acid, hydrochloric acid, phosphoric acid, phosphorus acid and sulfuric acid.

6. The composition of claim 1 wherein the biocompatible acid is an organic acid.

7. The composition of claim 6, wherein the organic acid is acetic acid.

8. A tissue implant suitable for treating an injury or a medical condition in a human comprising a matrix of digested allogeneic human muscle.

9. The implant of claim 8, wherein said matrix of digested allogeneic human muscle comprises from about 1% to about 100% of the final weight of said implant.

10. The implant of claim 9, wherein said matrix of digested allogeneic human muscle comprises from 15% to about 95% of the weight of said tissue implant.

11. The implant of claim 10, wherein said matrix of digested allogeneic human muscle comprises from 25% to about 85% of the weight of said tissue implant.

12. The implant of claim 8, further comprising demineralized bone matrix (DBM).

13. The implant of claim 12, wherein said DBM is uniformly distributed throughout the matrix.

14. The implant of claim 12, wherein said DBM is layered within said matrix.

15. The implant of claim 8, further comprising cortical cancellous chips (CCC).

16. The implant of claim 15, wherein said CCC is uniformly distributed throughout the matrix.

17. The implant of claim 15, wherein said CCC is layered within said matrix.

18. The implant of claim 8 further comprising digested allogeneic human tendon.

19. A method for making a muscle tissue slurry comprising the steps of:
   i. removing the fat and soluble proteins from allogeneic or xenographic mammalian muscle tissue;

ii. lyophilizing the muscle tissue from step (i);
iii. shredding the lyophilized muscle tissue; and
iv. mixing the shredded muscle tissue in an aqueous carrier to form a muscle tissue slurry having a viscosity within the range of 1 centistoke to 20,000 centistoke.

20. A method for making an implantable tissue comprising the steps of:
   i. removing the fat and soluble proteins from allogeneic or xenographic mammalian muscle tissue;
   ii. lyophilizing the muscle tissue from step (i);
   iii. shredding the lyophilized muscle tissue;
   iv. mixing the shredded muscle tissue in an aqueous carrier to form a muscle tissue slurry having a viscosity within the range of 1 centistoke to 20,000 centistokes;
   v. transferring the muscle tissue slurry to an appropriate shaped mold; and
   vi. drying the slurry in the mold to form the correspondingly shaped tissue implant.

21. The method of claim 20, wherein the aqueous carrier comprises a biocompatible acid.

* * * * *